United States Patent [19]

Kogure et al.

[11] 4,007,217
[45] Feb. 8, 1977

[54] PROCESS FOR PRODUCING 2-HYDROXY-3-BUTENOIC ACID DERIVATIVES

[75] Inventors: Katsura Kogure, Kawagoe; Noriyoshi Sueda, Tokyo; Sizuo Himoto, Kawagoe; Youziro Yoshino, Tokyo; Kunio Nakagawa, Kawagoe, all of Japan

[73] Assignee: Nisshin Flour Milling Co., Ltd., Nihonba, Japan

[22] Filed: July 28, 1975

[21] Appl. No.: 599,776

[30] Foreign Application Priority Data

July 27, 1974 Japan .............................. 49-85621

[52] U.S. Cl. ..................... 260/473 A; 260/348.6; 260/468 K; 260/471 R; 260/473 F; 260/484 R
[51] Int. Cl.² ......................................... C07C 69/76
[58] Field of Search ....... 260/473 A, 484 R, 468 X, 260/468 L

[56] References Cited
UNITED STATES PATENTS 3,925,458  12/1975  Kogure et al. ................. 260/473 A Primary Examiner—Paul J. Killos

[57] ABSTRACT

Process for producing a 2-hydroxy-3-butenoic acid derivative having the formula

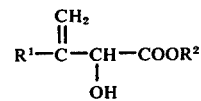

wherein $R^1$ is an aliphatic, alicyclic or aromatic group and $R^2$ is a lower alkyl group by treating a glycidic acid ester derivative having the formula

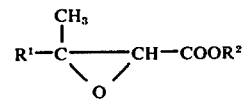

wherein $R^1$ and $R^2$ are as defined above in the presence of an acid.

4 Claims, No Drawings

PROCESS FOR PRODUCING 2-HYDROXY-3-BUTENOIC ACID DERIVATIVES

This invention relates to a process for producing a novel 2-hydroxy-3-butenoic acid derivative.

According to the present invention, a compound of the formula (II),

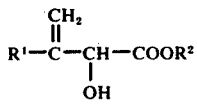

wherein $R^1$ is an aliphatic, alicyclic or aromatic group and $R^2$ is a lower alkyl group, can be obtained in a high yield by treating a glycidic acid ester derivative of the formula (I),

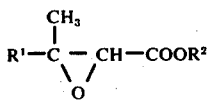

wherein $R^1$ and $R^2$ are as defined above, in the presence of an acid at a temperature of about 0° to 100° C.

The compound that is used as the starting material in the present invention is a compound of the aforesaid formula (I), wherein $R^2$ is a lower alkyl group, e.g. methyl, ethyl, n-propyl, isopropyl, n-butyl, tert-butyl, isobutyl or the like alkyl group having up to 4 carbon atoms, and $R^1$ is an alkyl (saturated or unsaturated, straight chain or branched-chain alkyl), cycloalkyl or aryl (including alkaryl and aralkyl) group. Concrete examples of the group represented by $R^1$ are methyl, ethyl, propyl, isopropyl, n-butyl, sec-butyl, tert-butyl, amyl, hexyl, heptyl, octyl, decyl, dodecyl, octadecyl, vinyl, allyl, methallyl, butenyl, pentenyl, hexenyl, heptenyl, octenyl, ethynyl, propinyl, cyclobutyl, cyclopentyl, cyclohexyl, methylcyclohexyl, cycloheptyl, cyclooctyl, cyclodecyl, cycloundecyl, cyclododecyl, cyclopentadecyl, phenyl, tolyl, xylyl, benzyl, phenetyl, phenylpropyl, naphthylmethyl, o-carboxybenzyl, and condensed and crosslinked ring structure groups such as indanyl, indenyl, naphthyl, phenanthryl, cyclopentano-polyhydrophenanthryl, adamantanyl, bicyclo(3:1:1)heptyl and bicyclo(2:2:2)octyl. All these groups may be unsubstituted or may be substituted by one or more incoherent substituents. Examples of such substituents are alkoxy groups such as methoxy, ethoxy, propoxy and butoxy; acyloxy groups such as acetoxy, propionoxy and butyroxy; nitro groups; alkylamino groups such as dimethylamino; and halogens such as fluorine, chlorine and bromine. Particularly important as the groups represented by $R^1$ are p-alkylphenyls including p-methylphenyl; 4-biphenylyl; 4-cyclohexylphenyl; 3-phenoxyphenyl; 4'-fluoro-4-biphenylyl; 2-fluoro-4-biphenylyl; 3-benzoylphenyl; and 6-methoxy-2-naphthyl.

Examples of the acid used in the reaction are such inorganic and organic acids as sulfuric acid, hydrogen chloride, phosphoric acid and p-toluenesulfonic acid. The amount of the acid used is from about 1/40 to 1/5 mole per mole of the starting material, but when the acid is used in an amount of about 1/30–1/10 mole per mole of the starting material, the end compound can be obtained in an extremely high yield. The reaction should be effected in the substantial absence of water, but may be carried out in the presence of an anhydrous solvent. Examples of the anhydrous solvent are nonprotonic organic solvents such as dimethyl sulfoxide, dimethyl formamide, ether, benzene and hexane. The reaction proceeds smoothly at a temperature in the range from 0° to 100° C., but is conveniently carried out at room temperature. The reaction time is in the range from 30 minutes to 20 hours, but the reaction substantially terminates within about 2 hours.

The product of the present invention, obtained in the above-mentioned manner, is useful as a novel intermediate for synthesizing homologues of the conventional antiphlogistic known as "ibuprofen". That is, the product 2-hydroxy-3-butenoic acid derivative of the aforesaid formula (II) is treated with an acid to prepare a propionaldehyde of the general formula

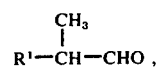

wherein $R^1$ is as defined previously, and the thus prepared propionaldehyde is further oxidized, whereby an ibuprofentype compound of the general formula

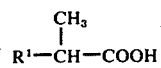

can be obtained. Alternatively, the compound of the aforesaid formula (II) may be hydrolyzed to a corresponding 2-hydroxy-3-butenoic acid or its salt, and then treated in the same manner as above.

The compound of the aforesaid formula (I), which is used as the starting material in the present invention, can be prepared by, for example, reacting an acetophenone derivative of the formula $R^1$—$COCH_3$, wherein $R^1$ is as defined previously, with an α-halogenated acetic acid ester of the formula $XCH_2CO_2R^2$, wherein $R^2$ is as defined previously; and X is a halogen atom. This reaction is preferably carried out under the conditions of Darzens' condensation, i.e. in an inert gas atmosphere under anhydrous conditions in the presence of an alkali condensing agent. As the condensing agent, there may be used sodium methoxide, sodium ethoxide, sodium isopropoxide or sodium amide.

The present invention is illustrated below with reference to examples, but the invention is not limited to the examples.

EXAMPLE 1

Production of methyl 2-hydroxy-3-(4-isobutylphenyl)-3-butenoate

To a stirred mixture of 54.0 g. of 4-isobutylacetophenone and 65.0 g. of methyl chloroacetate, 30.0 g. of sodium methoxide was gradually added over a period of 3 hours in a nitrogen current at below 5° C. The resulting mixture was brought back to room temperature, and then stirred overnight. Thereafter, the mixture was elevated in temperature to 80° to 90° C. and further stirred at said temperature for 1.5 hours. After cooling, the reaction liquid was incorporated with ether, washed with water and then dried. Subsequently, the ether was evaporated, and the residue was subjected to distillation to obtain 61.0 g. of methyl 3-methyl-3-(4-isobutylphenyl)-glycidate, b.p. 108°–112° C./0.2 mmHg, yield 80.0% (theoretical value).

32.2 Grams of the methyl 3-methyl-3-(4-isobutylphenyl)-glycidate was dissolved in 90 ml. of dry isopropyl ether. Into this solution, 0.7 g. of sulfuric acid was dropped with ice-cooling, and the resulting mixture was reacted at room temperature for 1 hour. Thereafter, the reaction liquid was poured into water, and then extracted with isopropyl ether. The isopropyl ether layer was washed with water and with a saturated aqueous sodium chloride solution in this order, and then dried over anhydrous magnesium sulfate. Subsequently, the isopropyl ether was evaporated under reduced pressure, and the residue was subjected to distillation to obtain 29.0 g. of the end compound, b.p. 113°–115° C./0.2 mmHg, yield 90% (theoretical value).

Elementary analysis (for $C_{15}H_{20}O_3$): Calculated (%): C 72.55, H 8.12; Found (%): C 71.99, H 8.18.

EXAMPLE 2

32.2 Grams of methyl 3-methyl-3-(4-isobutylphenyl)-glycidate was dissolved in 150 ml. of dry dimethyl sulfoxide. Into this solution, 0.7 g. of sulfuric acid was dropped with ice-cooling, and the resulting mixture was reacted at room temperature for 1 hour. Thereafter, the reaction liquid was poured into water, and then extracted with ether. The ether layer was washed with water and with a saturated aqueous sodium chloride solution in this order, and then dried over anhydrous magnesium sulfate. Subsequently, the ether was evaporated under reduced pressure, and the residue was subjected to distillation to obtain 29.3 g. of the end compound, b.p. 113°–115° C./0.2 mmHg, yield 91% (theoretical value).

Elementary analysis (for $C_{15}H_{20}O_3$): Calculated (%): C 72.55, H 8.12; Found (%): C 72.34, H 8.16.

EXAMPLE 32.2 Grams of methyl 3-methyl-3-(4-isobutylphenyl)-glycidlate was dissolved in 150 ml. of dry dimethyl fomamide. Into this solution, 0.7 g. of sulfuric acid was dropped with ice-cooling, and the resulting mixture was reacted at room temperature for 1 hour. Thereafter, the reaction liquid was poured into water, and then extracted with ether. The ether layer was washed with water and with a saturated aqueous sodium chloride solution in this order, and then dried over anhydrous magnesium sulfate. Subsequently, the ether was evaporated under reduced pressure, and the residue was subjected to distillation to obtain 27 g. of the end compound, b.p. 113°–115° C./0.2 mmHg, yield 84% (theoretical value).

EXAMPLE 4

Production of ethyl 2-hydroxy-3-(4-t-butylphenyl)-3-butenoate

To a stirred mixture of 26.4 g. of 4-t-butylacetophenone and 16.2 g. of ethyl chloroacetate, 10.2 g. of sodium ethoxide was gradually added over a period of 30 minutes at 10° to 15° C. The resulting mixture was brought back to room temperature, and then stirred overnight. Thereafter, the reaction liquid was elevated in temperature to 85° C., and further stirred at said temperature for 1.5 hours. After cooling, the mixture was incorporated with ether, washed with water and then dried. Subsequently, the ether was evaporated, and the residue was subjected to distillation to obtain 25.0 g. of ethyl 3-methyl-3-(4-t-butylphenyl)-glycidate, b.p. 108°–111° C./0.2 mmHg, yield 67% (theoretical value).

12.4 Grams of the ethyl 3-methyl-3-(4-t-butylphenyl-glycidate was dissolved in 60 ml. of dry isopropyl ether. Into this solution, 0.3 g. of sulfuric acid was dropped with ice-cooling, and the resulting mixture was reacted at room temperature for 1 hour. Thereafter, the reaction liquid was poured into water, and then extracted with ether. The ether layer was washed with water and with a saturated aqueous sodium chloride solution in this order, and then dried over anhydrous magnesium sulfate. Subsequently, the ether was evaporated under reduced pressure, and the residue was subjected to distillation to obtain 9.7 g. of the end compound, b.p. 115°–119° C./0.2 mmHg, yield 78.2% (theoretical value).

Elementary analysis (for $C_{16}H_{22}O_3$): Calculated (%): C 73.25, H 8.45; Found (%): C 72.91, H 8.60.

EXAMPLE 5

12.4 Grams of ethyl 3-methyl-3-(4t -butylphenyl)-glycidate was dissolved in 60 ml. of dry dimethyl formamide. Into this solution, 0.5 g. of sulfuric acid was dropped with ice-cooling, and the resulting mixture was reacted at room temperature for 2 hours. Thereafter, the reaction liquid was poured into water, and then extracted with ether. The ether layer was washed with water and with a saturated aqueous sodium chloride solution in this order, and then dried over anhydrous magnesium sulfate. Subsequently, the ether was evaporated under reduced pressure, and the residue was subjected to distillation to obtain 10.4 g. of ethyl 2-hydroxy-3-(4-t-butylphenyl)-3-butenoate, b.p. 115°–119° C./0.2 mmHg, yield 84% (theoretical value).

EXAMPLE 6

Methyl 2-hydroxy-3-(4-cyclohexylphenyl)-3-butenoate

40 Grams of 4-cyclohexylacetophenone and 43.2 g. of methyl chloroacetate were dissolved in a mixed solvent comprising 50 ml. of n-hexane and 50 ml. of benzene. To this solution, 27.8 g. of sodium methoxide was gradually added over a period of 1 hour with vigorous stirring in a nitrogen current at below 5° C. The resulting mixture was stirred at 5° C. for 2 hours and at room temperature for 1 hour, and then heated and refluxed with stirring for 30 minutes. After cooling, the reaction liquid was incorporated with hexane, and the organic layer was washed with water and then dried. Thereafter, the organic solvent was evaporated under reduced pressure to obtain 50 g. of methyl 3-methyl-3-(4-cyclohexylphenyl)-glycidate, yield 91% (theoretical value from the 4-cyclohexylacetophenone).

IR (cm$^{-1}$): 1755, 1735, 1210, 836.

NMR (δ ppm): 1.73 (3H, s, —C(CH₃)—C—), 3.80, 3.42 (3H, s, s, —CO₂CH₃), 3.45, 3.63 (1H, s, s, —C(H)—).

50 Grams of the methyl 3-methyl-3-(4-cyclohexylphenyl)-glycidate was dissolved in 300 ml. of dry isopropyl ether. Into this solution, 0.6 g. of concentrated sulfuric acid was dropped with stirring and ice-cooling, and the resulting mixture was stirred at room temperature for 2 hours. Thereafter, the reaction liquid was poured into water, and then extracted with isopropyl ether. The isopropyl ether layer was recovered, and the aqueous layer was extracted with isopropyl ether. Subsequently, the two extracts were combined together, washed with water and then dried over anhydrous magnesium sulfate to obtain 42 g. of methyl 2-hydroxy-3-(4-cyclohexylphenyl)-3-butenoate, yield 84% (theoretical value).

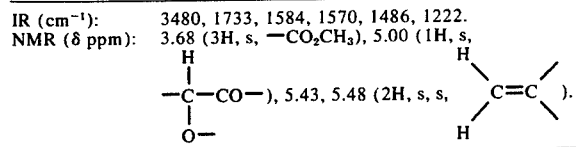

Elementary analysis (for $C_{17}H_{22}O_3$): Calculated (%): C 74.42, H 8.08; Found (%): C 74.16, H 8.23.

EXAMPLE 7

Methyl 2-hydroxy-3-(3-phenoxyphenyl)-3-butenoate 19.4 Grams of 3-phenoxyacetophenone and 21.6 g. of methyl chloroacetate were dissolved in 40 ml. of benzene. To this solution, 13.9 g. of sodium methoxide was gradually added over a period of 1 hour with vigorous stirring in a nitrogen current at 5° to 6° C. The resulting mixture was stirred at said temperature for 1 hour and at room temperature for additional 1 hour, and then heated and refluxed with stirring for 1 hour. After cooling, the reaction liquid was incorporated with benzene and water, and then extracted with benzene. The benzene layer was washed with water and dried over anhydrous sodium sulfate, and then the benzene was evaporated under reduced pressure to obtain 21.0 g. of methyl 3-methyl-3-(3-phenoxyphenyl)-glycidate, yield 81%.

IR ($cm^{-1}$): 1745, 1730, 1580, 1228.

NMR ($\delta$ ppm): 1.68, 1.72 (3H, s, s, $-\overset{CH_3}{\underset{|}{C}}-$), 3.47, 3.79 (3H, s, s, $-CO_2CH_3$), 3.42, 3.63

(1H, s, s, $-\overset{|}{\underset{H}{C}}-$).

8.0 Grams of the methyl 3-methyl-3-(3-phenoxyphenyl)-glycidate was dissolved in 100 ml. of dimethyl sulfoxide. To this solution, 0.3 g. of concentrated sulfuric acid was added with stirring and ice-cooling, and the resulting mixture was stirred at room temperature for 20 hours. Thereafter, the reaction liquid was poured into water, and then extracted with ethyl acetate. The ethyl acetate layer was washed successively with water, an aqueous sodium bicarbonate solution and water in this order, and then dried over anhydrous magnesium sulfate. Subsequently, the ethyl acetate was evaporated under reduced pressure, and 8.0 g. of the residue was purified according to silica gel column chromatography to obtain 4.7 g. of methyl 2-hydroxy-3-(3-phenoxyphenyl)-3-butenoate, yield 59% (theoretical value).

IR ($cm^{-1}$): 3480, 1733, 1584, 1570, 1486, 1222.

NMR ($\delta$ ppm): 3.68 (3H, s, $-CO_2CH_3$), 5.00 (1H, s, $-\overset{H}{\underset{\underset{O-}{|}}{C}}-CO-$), 5.43, 5.48 (2H, s, s, $\overset{H}{\underset{H}{\diagdown}}C=C\overset{\diagup}{\diagdown}$).

Elementary analysis (for $C_{17}H_{16}O_4$): Calculated (%): C 71.82, H 5.67; Found (%): C 71.58, H 5.49.

EXAMPLE 8

Methyl 2-hydroxy-3-(2-fluoro-4-biphenylyl)-3-butenoate 19.0 Grams of 4-acetyl-2-fluorobiphenyl and 19.2 g. of methyl chloroacetate were dissolved in a mixed solvent comprising 40 ml. of benzene and 20 ml. of dimethyl formamide. To this solution, 10.6 of sodium methoxide was gradually added over a period of 1 hour with vigorous stirring in a nitrogen current at below 8°C. The resulting mixture was stirred at 10° C. for 1 hour, at 25° C. for 1 hour and then at 60° C. for 1 hour. After cooling, the reaction liquid was incorporated with benzene and water, and then extracted with benzene. The benzene layer was washed with water and dried over anhydrous magnesium sulfate, and then the benzene was evaporated under reduced pressure to obtain 20.2 g. of methyl 3-methyl-3-(2-fluoro-4-biphenylyl)glycidate, yield 79% (theoretical value).

20.2 Grams of the methyl 3-methyl-3-(2-fluoro-4-biphenylyl)-glycidate was dissolved in a mixed solvent comprising 60 ml. of dimethyl sulfoxide and 40 ml. of benzene. To this solution, 0.2 ml. of concentrated sulfuric acid was added with ice-cooling, and the resulting mixture was stirred at room temperature for 2 hours. Thereafter, the reaction liquid was poured into water, and then extracted with benzene. The benzene layer was washed successively with water, an aqueous sodium bicarbonate solution and water in this order, and then dried over anhydrous magnesium sulfate. Subsequently, the benzene was evaporated under reduced pressure to obtain 8.4 g. of oily methyl 2-hydroxy-3-(2-fluoro-4-biphenylyl)-3-butenoate, yield 92%.

Elementary analysis (for $C_{17}H_{15}FO_3$ (286)): Calculated (%): C 71.32, H 5.28; Found (%): C 71.11, H 5.40.

EXAMPLE 9

Methyl 2-hydroxy-3-(4-biphenylyl)-3-butenoate 14.0 Grams of 4-acetylbiphenyl and 15.4 g. of methyl chloroacetate were dissolved in a mixed solvent comprising 30 ml. of benzene and 30 ml. of ether. To this solution, 8.5 g. of sodium methoxide was gradually added over a period of 30 minutes with vigorous stirring in a nitrogen current at below 8° C. The resulting mixture was stirred at 10° C. for 1 hour and at 25° C. for 1 hour, and then at reflux temperature for 1 hour. After cooling, the reaction liquid was incorporated with ether, washed with water and then dried. Subsequently, the organic solvent was evaporated under reduced pressure to obtain 15.0 g. of powdery methyl 3-methyl-3-(4-biphenylyl)-glycidate, m.p. 74.7°–77.0° C.

IR ($cm^{-1}$): 1748, 1208, 1081, 770.

| | |
|---|---|
| NMR (δ ppm): | 1.77, 1.79 (3H, s, s, —C(CH₃)—), 3.46, |
| | 3.82 (3H, s, s, —CO₂CH₃), 3.50, 3.70 |
| | (1H, s, s, —C(H)—). |

8.0 Grams of the methyl 3-methyl-3-(4-biphenylyl)-glycidate was dissolved in a mixed solvent comprising 30 ml. of dimethyl formamide and 20 ml. of benzene. To this solution, 0.1 g. of concentrated sulfuric acid was added with ice-cooling, and the resulting mixture was stirred at room temperature for 3 hours. Thereafter, the reaction liquid was poured into water, and then extracted with benzene. The benzene layer was washed succeessively with water, an aqueous sodium bicarbonate solution and water in this order, and then dried over anhydrous magnesium sulfate. Subsequently, the benzene was evaporated under reduced pressure to obtain 6.8 g. of methyl 2-hydroxy-3-(4-biphenylyl)-3-butenoate, yield 85% (theoretical value).

| | |
|---|---|
| IR (cm⁻¹): | 3460, 1731, 1596, 1242, 1208, 1112, 1078, 843. |
| NMR (δ ppm): | 3.72 (3H, s, —CO₂CH₃), 5.10 (1H, s, —C(H)(O—)—CO—), 5.44, 5.56 (2H, s, s, C=C(H)(H)). |

Elementary analysis (for C₁₇H₁₆O₃):
Calculated (%): C 76.10, H 6.01; Found (%): C 75.95, H 6.20.

EXAMPLE 10

Ethyl 2-hydroxy-3-(3-benzoylphenyl)-3-butenoate 15.0 Grams of ethyl 3-methyl-3-(3-benzoylphenyl)-glycidate was dissolved in 100 ml. of benzene. To this solution, 0.1 ml. of concentrated sulfuric acid was added, and the resulting mixture was stirred at room temperature for 2 hours. After completion of the reaction, the reaction liquid was charged with 100 ml. of benzene, and then transferred to a separating funnel. The benzene layer was washed successively with water, an aqueous sodium bicarbonate solution and water in this order, and then dried over anhydrous magnesium sulfate. Subsequently, the benzene was evaporated under reduced pressure, and the residue was purified according to silica gel column chromatography to obtain 9.2 g. of ethyl 2-hydroxy-3-(3-benzoylphenyl)-3-butenoate, yield 61%.

Elementary analysis (for C₁₉H₁₈O₄): Calculated (%): C 75.53, H 5.85; Found (%): C 75.19, H 5.61.

EXAMPLE 11

Methyl 2-hydroxy-3-(4'-fluoro-4-biphenylyl)-3-butenoate 9.5 Grams of 4-acetyl-4'-fluorobiphenyl and 9.6 g. of methyl chloroacetate were dissolved in a mixed solvent comprising 20 ml. of benzene and 10 ml. of dimethyl formamide. To this solution, 5.3 g. of sodium methoxide was gradually added over a period of 30 minutes with vigorous stirring in a nitrogen current at below 8° C. The resulting mixture was stirred at 10° C. for 1 hour, at 25° C. for 1 hour and then at 60° C. for 1 hour. After cooling, the reaction liquid was incorporated with benzene and water, and extracted with benzene. The benzene layer was washed with water and dried over anhydrous magnesium sulfate, and then the benzene was evaporated under reduced pressure to obtain 10.1 g. of powdery methyl 3-methyl-3-(4'-fluoro-4-biphenylyl)-glycidate, m.p. 68.6°–70.2° C., yield 79% (theoretical value).

| | |
|---|---|
| IR (cm⁻¹): | 1740, 1597, 1498, 1208, 823. |
| NMR (δ ppm): | 1.70, 1.73 (3H, s, s, —C(CH₃)—), 3.42, |
| | 3.77 (3H, s, s, —CO₂CH₃), 3.42, 3.65 |
| | (1H, s, s, —C(H)—). |

9.0 Grams of the methyl 3-methyl-3-(4'-fluoro-4-biphenylyl)-glycidate was dissolved in 100 ml. of benzene. To this solution, 0.15 g. of concentrated sulfuric acid was added with ice-cooling, and the resulting mixture was stirred at room temperature for 2 hours. Thereafter, the reaction liquid was poured into water, and then extracted with benzene. The benzene layer was washed successively with water, an aqueous sodium bicarbonate solution and water in this order, and then dried over anhydrous magnesium sulfate. Subsequently, the benzene was evaporated under reduced pressure to obtain 8.5 g. of methyl 2-hydroxy-3-(4'-fluoro-4-biphenylyl)-3-butenoate, yield 94%.

| | |
|---|---|
| IR (cm⁻¹): | 3463, 1731, 1600, 1499, 1223, 1160, 831. |
| NMR (δ ppm): | 3.71 (3H, s, —CO₂CH₃), 5.08 (1H, s, —C(H)(O—)—CO—), 5.44, 5.55 (2H, s, s, C=C(H)(H)). |

Elementary analysis (for C₁₇H₁₅FO₃): Calculated (%): C 71.32, H 5.28; Found (%): C 71.16, H 5.11.

EXAMPLE 12

Isopropyl 2-hydroxy-3-(4-cyclohexylphenyl)-3-butenoate

20 Grams of 4-cyclohexylacetophenone and 26.5 g. of isopropyl chloroacetate were dissolved in 50 ml. of benzene. To this solution, 21 g. of sodium isopropoxide was gradually added over a period of 1 hour with vigorous stirring in a nitrogen current at below 5° C. The resulting mixture was stirred at 5° C. for 1 hour, at room temperature for 1 hour and then at reflux temperature for 1 hour. After cooling, the reaction liquid was incorporated with benzene and water, and extracted with benzene. The benzene layer was washed with water and dried over anhydrous sodium sulfate, and then the benzene was evaporated under reduced pressure.

The resulting isopropyl 3-methyl-3-(4-cyclohexylphenyl)-glycidate was dissolved in 200 ml. of isopropyl ether. To this solution, 0.3 g. of concentrated sulfuric acid was gradually added with ice-cooling, and the resulting mixture was stirred at room temperature for 4 hours. Thereafter, the reaction liquid was poured into water, and then extracted with isopropyl ether. The isopropyl ether layer was washed with water and dried, and then the isopropyl ether was evaporated under reduced pressure to obtain 23 g. of pale yellow, oily isopropyl 2-hydroxy-3-(4-cyclohexylphenyl)-3-butenoate, yield 76%.

Elementary analysis (for $C_{19}H_{26}O_3$): Calculated (%): C 75.46, H 8.67; Found (%): C 75.40, H 8.39.

EXAMPLE 13

Ethyl 2-hydroxy-3-(4-biphenylyl)-3-butenoate 14.0 Grams of 4-acetylbiphenyl and 16.4 g. of ethyl chloroacetate were dissolved in a mixed solvent comprising 60 ml. of benzene and 30 ml. of ether. To this solution, 10.7 g. of sodium ethoxide was gradually added over a period of 30 minutes with vigorous stirring in a nitrogen current at below 8° C. The resulting mixture was stirred at 10° C. for 1 hour, at 25° C. for 1 hour and then at reflux temperature for 1 hour. After cooling, the reaction liquid was incorporated with ether, and the organic layer was washed with water and dried. Subsequently, the organic solvent was evaporated under reduced pressure to obtain 16.0 g. of ethyl 3-methyl-3-(4-biphenylyl)-glycidate.

16.0 Grams of the ethyl 3-methyl-3-(4-biphenylyl)-glycidate was dissolved in 200 ml. of ethyl ether. To this solution, 0.2 g. of concentrated sulfuric acid was added with stirring and cooling, and the resulting mixture was stirred at room temperature for 4 hours. Thereafter, the reaction liquid was poured into water, and then extracted with ether. The ether layer was washed successively with water, an aqueous sodium bicarbonate solution and water in this order, and then dried over anhydrous magnesium sulfate. Subsequently, the ether was evaporated under reduced pressure to obtain 13.9 g. of ethyl 2-hydroxy-3-(4-biphenylyl)-3-butenoate, yield 86%.

Elementary analysis (for $C_{18}H_{18}O_3$): Calculated (%): C 76.57, H 6.43; Found (%): C 76.48, H 6.29

EXAMPLE 14

Methyl 2-hydroxy-3-(6-methoxy-2-naphthyl)-3-butenoate 8.3 Grams of 6-methoxy-2-acetylnaphthalene and 8.3 g. of methyl chloroacetate were dissolved in 50 ml. of anhydrous benzene. To this solution, 4.1 g. of sodium methoxide was gradually added over a period of 1.5 hours with stirring in a nitrogen current at below 5° C. The resulting mixture was stirred at 5° C. for 1 hour, at room temperature for 1 hour and then at 75° C. for 1 hour. After cooling, the reaction liquid was incorporated with water and ethyl acetate, and then sufficiently stirred. The organic layer was recovered, washed with water and then dried over anhydrous magnesium sulfate. Subsequently, the organic solvent was evaporated under reduced pressure, and the resulting crude crystals were recrystallized from ethanol to obtain 7.2 g. of methyl 3-methyl-3-(6-methoxy-2-naphthyl)-glycidate, m.p. 123.8° C.–125.9° C., yield 68%.

Elementary analysis (for $C_{16}H_{16}O_4$): Calculated (%): C 70.57, H 5.92; Found (%): C 70.29, H 5.80.

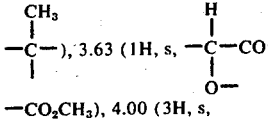

7.2 Grams of the methyl 3-methyl-3-(6-methoxy-2-naphthyl)-glycidate was dissolved in 50 ml. of benzene. To this solution, 0.2 g. of concentrated sulfuric acid was added with stirring at 10° C., and the resulting mixture was stirred at room temperature for 2 hours. Thereafter, the reaction liquid was charged with benzene and water, and extracted with benzene. The benzene layer was washed successively with water, an aqueous sodium bicarbonate solution and water in this order, and then dried over anhydrous magnesium sulfate. Subsequently, the benzene was evaporated under reduced pressure, and the resulting crude crystals were recrystallized from ethanol to obtain 6.1 g. of methyl 2-hydroxy-3-(6-methoxy-2-naphthyl)-3-butenoate, m.p. 90.6°–92.5° C., yield 85%.

Elementary analysis (for $C_{16}H_{16}O_4$): Calculated (%): C 70.57, H 5.92; Found (%): C 70.49, H 6.11.

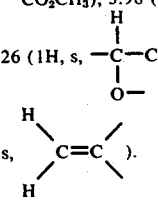

EXAMPLE 15

Methyl 2-hydroxy-3-(4-biphenylyl)-3-butenoate 3.0 Grams of methyl 3-methyl-3-(4-biphenylyl)-glycidate was dissolved in 30 ml. of isopropyl ether. To this solution, 0.3 g of p-toluenesulfonic acid was added, and the resulting mixture was stirred at 25° to 30° C. for 90 minutes. Thereafter, the reaction liquid was charged with 100 ml. of isopropyl ether, and then transferred to a separating funnel. The isopropyl ether layer was washed successively with water, an aqueous sodium bicarbonate solution and water in this order, and then dried over anhydrous magnesium sulfate. Subsequently, the isopropyl ether was evaporated under reduced pressure to obtain 2.7 g. of methyl 2-hydroxy-3-(4-biphenylyl)-3-butenoate, yield 90%.

Elementary analysis (for $C_{17}H_{16}O_3$): Calculated (%): C 76.10, H 6.01; Found (%): C 75.95, H 6.25.

EXAMPLE 16

Propyl 2-hydroxy-3-(4-cyclohexylphenyl)-3-butenoate 10.1 Grams of propyl 3-methyl-3-(4-cyclohexylphenyl)-glycidate was dissolved in 100 ml. of benzene. To this solution, 0.2 ml. of 105% polyphosphoric acid was added, and the resulting mixture was stirred at room temperature for 2 hours. Thereafter, the reaction liquid was poured into water, and then extracted with benzene. The benzene layer was washed successively with water, an aqueous sodium bicarbonate solution and water in this order, and then dried over anhydrous magnesium sulfate. Subsequently, the benzene was evaporated under reduced pressure, and the residue was purified according to silica gel column chromatography to obtain 6.1 g. of propyl 2-hydroxy-3-(4-cyclohexylphenyl)-3-butenoate, yield 60%.

Elementary analysis (for $C_{19}H_{26}O_3$): Calculated (%): C 75.46, H 8.67; Found (%): C 75.71, H 8.44.

EXAMPLE 17

Methyl 2-hydroxy-3-(4'-fluoro-4-biphenylyl)-3-butenoate 5.7 Grams of methyl 3-methyl-3-(4'-fluoro-4-biphenylyl)-glycidate was dissolved in 100 ml. of ether. To this solution was added 0.3 g. of p-toluenesulfonic acid, and the resulting mixture was stirred at room temperature for 2 hours. Thereafter, the reaction liquid was poured into water, and then extracted with ether. The ether layer was washed successively with water, an aqueous sodium bicarbonate solution and water in this order, and then dried over anhydrous magnesium sulfate. Subsequently, the ether was evaporated under reduced pressure to obtain 4.9 g. of methyl 2-hydroxy-3-(4'-fluoro-4-biphenylyl)-3-butenoate, yield 86%.

Elementary analysis (for $C_{17}H_{15}FO_3$): Calculated (%): C 71.32 H 5.28 Found (%): C 71.51, H 5.40.

EXAMPLE 18

Methyl 2-hydroxy-3-(6-methoxy-2-naphthyl)-3-butenoate 9.2 Grams of methyl 3-methyl-3-(6-methoxy-2-naphthyl)-glycidate was dissolved in 100 ml. of benzene. Into this solution, hydrogen chloride gas was introduced with stirring at 78° C. After stirring for 1 hour, the reaction liquid was poured into ice water, and then extracted with benzene. The benzene layer was washed successively with water, an aqueous sodium bicarbonate solution and water in this order, and then dried over anhydrous magnesium sulfate. Subsequently, the benzene was evaporated under reduced pressure, and the residue was purified according to silica gel column chromatography to obtain crude crystals. The crude crystals were recrystallized from ethanol to obtain 4.5 g. of methyl 2-hydroxy-3-(6-methoxy-2-nephthyl)-3-butenoate, yield 49%.

Elementary analysis (for $C_{16}H_{16}O_4$): Calculated (%): C 70.57, H 5.92; Found (%): C 70.81, H 5.75.

What we claim is:

1. A process for producing a 2-hydroxy-3-butenoic acid ester of the general formula,

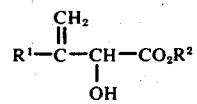

wherein $R^1$ is a radical selected from the group consisting of aliphatic, alicyclic and aromatic radicals and $R^2$ is a lower alkyl group, which comprises reacting in the absence of water and in the presence of inorganic or organic acid selected from the group consisting of sulfuric acid, hydrochloric acid, phosphoric acid and p-toluenesulfonic acid, a glycidic acid ester derivative of the general formula,

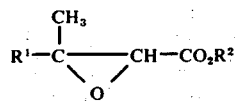

wherein $R^1$ and $R^2$ are as defined above and forming said 2-hydroxy-3-butenoic acid ester.

2. A process as defined in claim 1, wherein the glycidic acid ester is reacted in a substantially anhydrous state, optionally in a non-protonic organic solvent, at a temperature ranging from 0° C. to 100° C.

3. A process as defined in claim 1, wherein radical $R^1$ of the glycidic acid ester is selected from the group consisting of 4-lower alkylphenyl, 4-biphenylyl, 4-cyclohexylphenyl, 3-phenoxyphenyl, 4'-fluoro-4-biphenyl, 2-fluoro-4-biphenylyl, 3-benzoylphenyl and 6-methoxynaphthyl radicals.

4. A process as defined in claim 1 for producing a 2-hydroxy-3-(substituted aryl)-3-butenoic acid ester of the general formula,

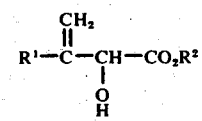

wherein $R^1$ is an aromatic radical and $R^2$ is a lower alkyl group from a glycidic acid ester derivative of the formula,

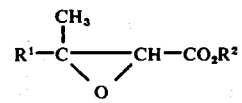

wherein $R^1$ and $R^2$ is as defined above.

* * * * *